United States Patent [19]

Young

[11] Patent Number: 4,522,644
[45] Date of Patent: Jun. 11, 1985

[54] METHOD FOR SELECTIVELY CONTROLLING PLANT SUCKERS

[75] Inventor: Donald C. Young, Fullerton, Calif.

[73] Assignee: Union Oil Company of California, Los Angeles, Calif.

[21] Appl. No.: 453,282

[22] Filed: Dec. 27, 1982

Related U.S. Application Data

[63] Continuation-in-part of Ser. No. 444,667, Nov. 26, 1982, , Continuation-in-part of Ser. No. 442,296, Nov. 17, 1982.

[51] Int. Cl.$^3$ ............................................. A01N 59/00
[52] U.S. Cl. ............................................ 71/78; 71/83
[58] Field of Search ...................................... 71/78, 83

[56] References Cited

U.S. PATENT DOCUMENTS

| | | | |
|---|---|---|---|
| 1,340,708 | 5/1920 | Fjellanger | 71/28 |
| 4,116,664 | 9/1978 | Jones | 71/28 |
| 4,318,343 | 1/1982 | Verdegaal et al. | 71/28 |

OTHER PUBLICATIONS

D. F. du Toit, Verslag Akad. Wetenschappen, 22, 573–4 (abstracted in Chemical Abstracts, 8, 2346, 1914).
L. H. Dalman, "Ternary Systems of Urea and Acids I, Urea, Nitric Acid and Water II, Urea, Sulfuric Acid and Water III, Urea, Oxalic Acid and Water"; JACS, 56, 549–53 (1934).
Sulfur Institute Bulletin No. 10 (1964) "Adding Plant Nutrient Sulfur to Fertilizers".

*Primary Examiner*—Catherine L. Mills
*Attorney, Agent, or Firm*—Dean Sandford; Gregory F. Wirzbicki; Michael H. Laird

[57] ABSTRACT

Methods for controlling parasitic plant suckers growing from desired vegetation are disclosed which involve selectively contacting the foliage of the plant sucker with an aqueous solution containing a urea-sulfuric acid component which is a reaction product of urea and sulfuric acid, and avoiding contact of the remaining foliage of the desired vegetation with the aqueous solution. The molar ratio of urea to sulfuric acid in the urea-sulfuric acid component is preferably within the range of about $\frac{1}{4}$ to about 7/4, and preferably at least about 25 percent of the sulfuric acid in the urea-sulfuric acid component is present as the monourea adduct of sulfuric acid. The aqueous solution may also contain an amount of a surfactant sufficient to increase the wetting ability of the solution for the foliage of the plant sucker to accentuate the herbicidal activity of the solution toward the plant sucker.

14 Claims, 1 Drawing Figure

METHOD FOR SELECTIVELY CONTROLLING PLANT SUCKERS

RELATED APPLICATIONS

This application is a continuation-in-part of my co-pending applications, Ser. No. 444,667, pending filed Nov. 26, 1982, for METHODS FOR CONTROLLING VEGETATION, and Ser. No. 442,296, pending filed Nov. 17, 1982 for SYSTEMIC HERBICIDAL COMPOSITIONS AND METHODS OF USE.

BACKGROUND OF THE INVENTION

1. Field of the Invention

This invention relates to methods of controlling parasitic or otherwise undesired vegetative growths from otherwise desirable plants, which undesirable growths are generally known as plant suckers, and particularly, the invention relates to the use of highly selective herbicidal methods for the selective control of plant suckers on desirable vegetation.

2. Description of the Art

A wide variety of ornamental and fruit bearing plants occasionally sprout undesirable and/or parasitic growths in addition to the established growth pattern of the plant. Such growths all known as plant suckers, so-called because they divert a significant portion of the plant's energy, and thus its ability to produce the desired fruit, flowers, or other ornamental growth. Plant suckers are nonbearing shoots, canes, or limbs that generally emanate from the lower portion of established desiduous, perenial fruit-bearing and ornamental trees and vines, and quite often emanate from the roots at some location other than the established main trunk of the tree or vine. However, plant suckers, in the sense that that term relates to the desirability or the undesirability of vegetative growth, are not necessarily limited to nonbearing growth. Quite often, established trees or vines produce additional bearing growth from their roots or lower main stem portions that is undesirable in that it does not contribute to the established growth pattern of the plant. Thus, such growth, even though it may ultimately bear fruit or ornamental vegetation, is often desirably eliminated.

The growth of plant suckers can occur on essentially all forms of vegetation, although it presents a significant problem primarily in commercial desiduous, perenial ornamental and fruit-bearing orchards and vineyards. The growth of plant suckers is a particularly significant and costly problem in orchards and vineyards in which the main vegetative growth is propagated from dissimilar root stock such as is the case with a variety of citrus, avacado, varietal grape, and other commercial crops. For instance, each year, plant suckers are ordinarily removed by hand from the lower stem portions or roots of varietal grapes shortly after vegetative growth recommences in the spring at a cost on the average of $80 per acre. The manual removal of plant suckers from citrus trees is also customarily practiced, although it is usually required less frequently, i.e., on the order of every 3 to 6 years.

The agricultural industry presently prefers to remove plant suckers manually due to the high potential for harm to the established trees or vines resulting from the use of available herbicides. Most fruit-bearing and ornamental groves and vineyards require years to reach a productive level. For instance, varietal grapes, citrus and avacados usually require at least three and sometimes as many as five years growth before they can produce a commercial crop. Accordingly, growers are understandably hesitant to use any method of sucker control other than manual removal that presents any significant risk of damage to the established plants.

Several contact herbicides are approved by the United States Environmental Protection Agency for use in the control of plant suckers and/or have been used for the control of such undesired growth. Maleic hydrazide (1,2-dihydropyridaziene-3,6-dione), a plant growth regulator, is used to retard sucker growth of tobacco plants. A mixture of n-octanol and n-decanol, sold under the tradename "Sucker Plucker", and the plant growth regulator sold under the name "Sucker Stymie" are also employed to inhibit and/or control sucker propagation in tobacco plants. Dinoseb, which contains the active ingredient 2-sec-butyl-4,6-dinitrophenol, is a contact herbicide which is infrequently used for sucker control in situations which present little risk of damage to existing vegetation. However, the potential toxicity of this compound to desired vegetation and the proximity of plant suckers to such desired vegetation make the use of this compound undesirable in most situations. Spray oils are sometimes employed in an attempt to control plant suckers but are generally not completely effective, possibly due to the fact that the plant sucker continues to be supported by the established plants' root system and therefore can receive energy and nutrients produced by photosynthesis in the unaffected portions of the established plant.

Sulfuric acid is approved for some applications by the U.S. Environmental Protection Agency, i.e., for the control of weeds in growing onions and garlic, and is an effective contact herbicide when applied in sufficient dosages. However, sulfuric acid is consumed by chemical reaction with plant foliage by oxidation and possibly by sulfonation reactions. Furthermore, sulfuric acid is very herbicidally active toward essentially all forms of vegetation which are not protected by a significant waxy cuticle coating. Thus, any over-spray onto the desired foliage of an existing plant, in most cases, will result in substantial damage to the foliage contacted.

Accordingly, a need exists for improved methods for controlling plant suckers that minimizes or eliminates these and other deficiencies associated with existing methods.

It is, therefore, a principal object of this invention to provide improved methods of controlling undesired growth from desired plants.

Another object is the provision of improved methods for controlling plant suckers.

Another object of this invention is the provision of methods for controlling plant suckers which are growing from established, desired vegetation, which methods are relatively nontoxic to the desired, established vegetation, to applicators, or to the environment.

Another object is the provision of methods which quickly and selectively eliminate plant suckers from established ornamental and fruit-bearing trees and vines while minimizing the possibility of damage to the established trees and vines.

Yet another object of this invention is the provision of methods for effectively controlling plant suckers and simultaneously adding significant amounts of plant nutrients and beneficial soil adjuvants to the plant environment.

Another object is the provision of methods for controlling plant suckers which methods are more efficient and are therefore less costly than previously available methods.

Other objects, aspects and advantages of this invention will be apparent to one skilled in the art in view of the following disclosure, the drawing, and the appended claims.

SUMMARY OF THE INVENTION

Briefly, the invention provides improved methods of controlling and eliminating plant suckers growing from desired plants without damaging the remainder of the desired plant by contacting the foliage of the plant sucker with a herbicidally effective amount of an aqueous solution containing a urea-sulfuric acid component in which the molar ratio of urea to sulfuric acid is within the range of about ¼ to about 7/4. The urea-sulfuric acid components employed in the methods of this invention are reaction products of urea and sulfuric acid containing the monourea adduct of sulfuric acid. A sufficient amount of the described aqueous solution is selectively applied to the foliage and stem of the plant sucker to eliminate the sucker from the remainder of the established plant, without contacting a significant amount of the aqueous solution with the foliage of the desired main portion of the plant. The applied aqueous solution may also contain an amount of a surfactant sufficient to increase the wetting ability of the solution for the foliage of the plant sucker. The foliage and stems of some plants are protected by a waxy cuticle coating, and surfactants significantly accentuate the activity of the urea-sulfuric acid component employed in the methods of this invention toward plants, the foliage of which is protected by such coatings.

The methods of this invention have several significant advantages over available alternatives including their ability to provide essentially immediate control and elimination of plant suckers while minimizing the risk of damage to the desired growth of the established plant from which the plant sucker propagated. The methods of this invention provide for specific contact herbicidal control of undesired plant suckers propagating from and in the immediate vicinity of desired established vegetation which methods do not produce any significant toxic symptoms in any part of the established vegetation other than in the parasitic sucker portion. In fact, the translocation of urea and sulfuric acid to the desired vegetative growth via the parasitic sucker, introduces nutrient nitrogen and sulfur to and enhances the growth of the desired vegetative growth.

The urea-sulfuric acid components employed in the methods of this invention can be applied directly to the woody parts of established vegetation without risk of toxicity to the established plants. Furthermore, the methods of this invention do not introduce any toxic compounds into the environment and they employ only materials that are relatively nontoxic and nonhazardous to applicators. The urea-sulfuric acid components employed in the methods of this invention are much less corrosive to human skin than is sulfuric acid. Yet, in aqueous solutions, the urea-sulfuric acid components are much more effective for the control of plant suckers than is sulfuric acid on an equivalent sulfuric acid weight basis. The herbicidal activity of the urea-sulfuric acid components employed in the methods of this invention can be increased even further by the addition of minor amounts of surfactants many of which are chemically unstable in the presence of free sulfuric acid.

Another particularly desirable aspect of the methods of this invention is that they contribute significant amounts of nutrient nitrogen and sulfur to the soil and they increase the availability of both the added nutrients and nutrients already present in the soil for the desired remaining crop plants, thus, they result in the improved growth of those plants.

While the described methods are more effective for the control of plant suckers than are methods employing sulfuric acid or other contact herbicides, they are also relatively safe in comparison to methods employing sulfuric acid and are much safer and have fewer ecotoxic effects than methods involving the use of other known contact herbicides. Furthermore, since the herbicidal activity of the urea-sulfuric acid components employed in the novel methods of this invention is not persistent, these methods can be used to control plant suckers growing on food crops without damaging the desired crop or introducing potentially toxic components into the food crop. The preferred urea-sulfuric acid compositions employed in the methods of this invention are also free of byproducts such as sulfamic acid and ammonium sulfamate that result from the decomposition of urea and/or sulfuric acid. Thus, these methods do not introduce such decomposition products into the environment or into the treated crop.

BRIEF DESCRIPTION OF THE DRAWING

This invention will be more readily understood by reference to the drawing which is a ternary-phase diagram of the urea, sulfuric acid, and water system illustrating isotherms at several different temperatures, the existence of three prominent eutectics along those isotherms, and the boundaries for the compositions employed in the methods of this invention

DETAILED DESCRIPTION OF THE INVENTION

Figure 1:
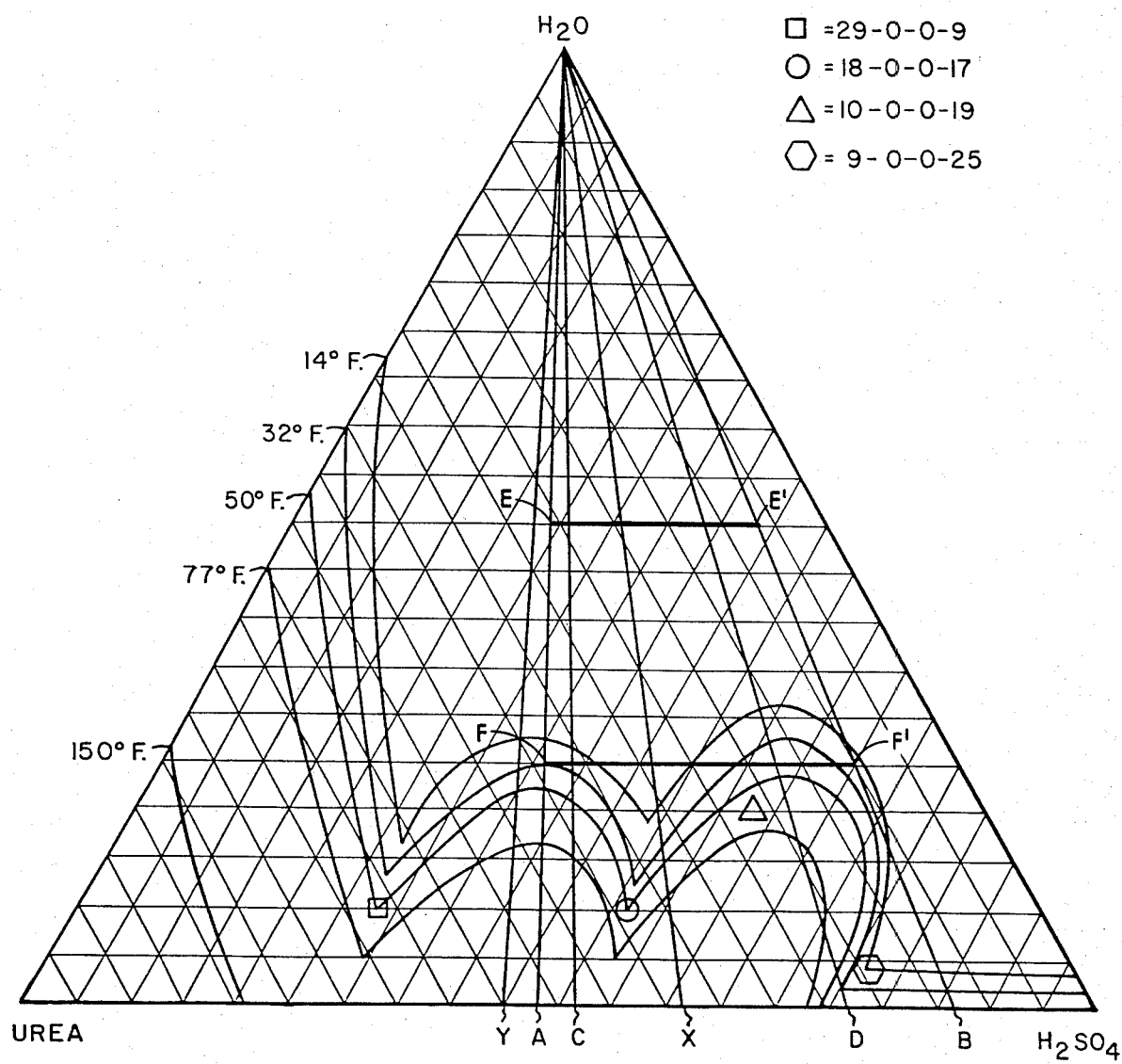

This invention provides novel methods for controlling and eliminating parasitic plant suckers by selectively contacting the plant sucker with an aqueous solution containing a urea-sulfuric acid component, which component comprises the monourea adduct of sulfuric acid. The urea-sulfuric acid components useful in the methods of this invention are reaction products of urea and sulfuric acid in which the molar ratio of urea to sulfuric acid is within the range of about ¼ to about 7/4 so that at least about 25 percent of the sulfuric acid is present as the monourea-sulfuric acid adduct. The aqueous solutions employed in the methods of this invention may also optionally contain a surfactant. Surfactants increase the wetting ability of the aqueous solution for the foliage of parasitic sucker growths and accentuate the herbicidal activity of the urea-sulfuric acid component. Contact of the aqueous urea-sulfuric acid solution with the foliage of the established plant which is not associated with the plant sucker is preferably avoided.

As used herein, the term "plant sucker" refers to undesired growth from the roots or lower extremities of established, perenial fruit-bearing or ornamental vegetation. The most significant and detrimental types of plant suckers in the agricultural industries are nonbearing shoots, canes or limbs that sprout from the lower stem or roots of cultivated fruit-bearing plants. While the methods of this invention can be employed to eliminate plant suckers from essentially all types of vegetation including both evergreen and deciduous plants, they are most advantageously employed to eliminate plant suckers that would otherwise reduce the growth and/or productivity of cultivated ornamental and fruit-bearing plants. The occurrence of plant suckers is particularly prevalent in deciduous perenial fruit-bearing and ornamental trees, bushes and cultivated vine crops. Thus, these methods are particularly useful for the elimination of plant suckers from such crops. Illustrative vine crops are grapes, including table grapes and varietal grapes, berry crops such as rasberries, blueberries, boysenberries, and the like. Illustrative deciduous, perenial tree crops include orchard crops such as citrus, apples, avacados, peach, nut fruits such as walnuts, almonds, etc., pears, apricots, and the like.

The methods of this invention are particularly suitable for the elimination of plant suckers from trellace-trained vine crops and established deciduous fruit trees, particularly such vine and tree crops that are grafted onto dissimilar root stock. A variety of tree and vine crops are grafted onto nonpreferred, dissimilar root stock to provide the resulting plant with resistance to disease such as fungus infestation to which the fruit-bearing portion of the plant would otherwise be susceptible. Illustrative cultivated crops that are often grafted to dissimilar root stock include citrus such as orange trees grafted from sour orange root stock, avacados, and varietal grapes. Varietal grapes such as chardonnay, columbard, zinfandel, cabernet, pinat noir, chenin blanc, and the like, table grapes such as Thompson seedless and concord grapes, and grapes grown for raisin production are sometimes grafted onto root stock that is more resistant to disease and fungus infestation than is the fruit-producing portion of the plant. The propagation of either bearing or nonbearing plant suckers from the dissimilar root stock is particularly undesirable in that the energy required for growth of the parasitic sucker deprives the fruit-bearing portion of the plant of energy required for fruit production. Similarly, the propagation of plant suckers from the lower stem portion of trellace-trained fruit vines of any type and from the lower trunk portion of cultivated fruit trees is undesirable in that it clutters the orchard or vineyard, disrupts the established pattern of plant growth and complicates fruit harvest.

The urea-sulfuric acid components employed in the methods of this invention are reaction products of urea and sulfuric acid containing the monourea adduct of sulfuric acid. Preferably, at least 25 percent of the sulfuric acid is present as the monourea-sulfuric acid adduct.

The four-digit composition designations used herein for the urea-sulfuric acid component, e.g., 18-0-0-17, are conventionally used in the agricultural industry to designate the concentration of nitrogen, phosphorus (as $P_2O_5$), potassium (as $K_2O$), and a fourth component in this case sulfur, expressed as the element. Thus, the composition 18-0-0-17 contains 18 weight percent nitrogen derived from urea and 17 weight percent sulfur derived from sulfuric acid. Using the atomic weights for nitrogen (14.01) and sulfur (32.07) and the molecular formulas and molecular weights for urea (60.06) and sulfuric acid (98.08), it can be determined that this composition has a urea/sulfuric acid molar ratio of 1.2 and contains 38.6 weight percent urea and 52.1 weight percent sulfuric acid. By difference, the composition contains 9.3 weight percent water. The concentrations of sulfuric acid and urea, and the urea/sulfuric acid molar ratios for all other compositions, can be determined by the same procedure.

The compositions and some crystallization temperatures of urea-sulfuric acid solutions useful in the methods of this invention are illustrated in the ternary phase diagram of the drawing. The phase diagram defines the relative proportions in weight percent for each of the three components—urea, sulfuric acid, and water at any point within the diagram. At each apex of the triangle the system consists completely of the indicated component. Thus, the urea concentration at the urea apex is 100 percent and diminishes linearly to 0 along a straight line from the urea apex to the $H_2O$—$HSO_4$ boundary line, i.e., the side of the triangle opposite the urea apex. The same is true of the remaining two components: water and sulfuric acid.

The diagram also illustrates the isotherms for the system at 14° F., 32° F., 50° F., 77° F., and 150° F. The 150° F. isotherm is illustrated only partially at the lower left-hand portion of the diagram. Each isotherm defines liquid compositions which, if cooled below the temperature indicated for the respective isotherm, will precipitate components of the system. However, the solutions will super-cool dramatically, e.g., by as much as 50° F., or more, under quiescent conditions in the absence of seed crystals, impurities, etc., that promote crystallization.

As indicated by the pattern of the isotherms, systems having a fixed ratio of urea to sulfuric acid become more stable at lower temperatures as the water concentration is increased. This is true throughout most of the phase diagram with the exception of the region in the vicinity of the higher acid eutectic in the lower right-hand portion of the phase diagram.

Three prominent eutectics are apparent within the region of the illustrated isotherms. Each eutectic represents a discontinuity in the response of the system, e.g., of crystallization point, to changes in solute concentration, and indicates the points of maximum solute concentration for a given isotherm in the regions of the phase diagram associated with those eutectics.

As indicated in the legend on the drawing, the left-hand eutectic on the 50° F. isotherm corresponds to the formulation 29-0-0-9. The middle eutectic on the same isotherm corresponds to the composition 18-0-0-17. The right-hand eutectic on the 14° F. isotherm corresponds to 9-0-0-25 which contains 19.3 weight percent urea, 76.6 weight percent sulfuric acid, and 4.1 weight percent water, and has a urea/sulfuric and molar ratio of 0.4. The composition intermediate the 50° F. and the 77° F. isotherms between the middle and right-hand eutectics indicated by a triangular designation corresponds to 10-0-0-19 which contains 21.5 weight percent urea, 55.2 weight percent sulfuric acid, and 23.3 weight percent water, and has a urea/sulfuric acid molar ratio of 0.6.

The bold horizontal lines E-E' and F-F' within the diagram prescribe the boundaries of concentrated urea-sulfuric acid compositions that are preferable from the standpoint of manufacture and packaging prior to dilution for use. Compositions falling below line E-E' have solute, i.e., urea and sulfuric acid, concentrations of 50 weight percent or higher. Compositions falling below line F-F' located at the 25 percent water line, contain 75 weight percent of a combination of urea and sulfuric acid, or more. It can be readily seen that the four specific compositions designated in the diagram contain more than 75 weight percent solute.

Bold lines running between the urea-sulfuric acid boundary (the lower boundary of the diagram) and the water apex, generally prescribe the operable and preferred urea-sulfuric component compositions employed in the methods of this invention. Line Y defines compositions having a 2/1 urea/sulfuric acid molar ratio. This line intersects the urea-sulfuric acid boundary at a point corresponding to approximately 55.0 weight percent urea. Compositions falling to the left of line Y do not contain any amount of the monourea-sulfuric acid adduct; they consist of combinations of the diurea adduct and excess urea. Such compositions have little or no contact herbicidal activity in comparison to the monourea adduct. Compositions falling to the right of line Y contain at least some of the monourea adduct, and the concentration of that adduct increases as the composition approaches line X. Compositions falling on line X have urea/$H_2SO_4$ molar ratios of 1/1 and correspond to those in which both the urea and sulfuric acid are present only as the monourea-sulfuric acid adduct. Line X intersects the urea-$H_2SO_4$ boundary at a urea concentration of 38.0 weight percent.

Compositions falling between lines A and B are those in which at least 25 percent of the sulfuric acid is present as the monourea-sulfuric acid adduct. In compositions falling on line A, 25 percent of the sulfuric acid is present as the monourea adduct and 75 percent is present as the diurea-sulfuric acid adduct. In compositions falling along line B, 25 percent of the sulfuric acid is present in the monourea adduct and 75 percent is present as free sulfuric acid. Line A intersects the urea-sulfuric acid boundary at a point corresponding to 51.9 weight percent urea; line B intersects the same boundary at the 13.2 weight percent urea level.

In compositions falling between lines C and D, at least 50 percent of the sulfuric acid is present as the monourea adduct. Line C defines compositions in which 50 percent of the sulfuric acid is present as the monourea adduct and 50 percent is present as the diurea-sulfuric acid adduct. Compositions falling on line D correspond to those in which 50 percent of the sulfuric acid is uncomplexed, free sulfuric acid. Lines C and D intersect the urea-sulfuric acid boundary at points corresponding to 47.9 and 23.4 weight percent urea, respectively.

The 18-0-0-17 composition, and close approximations such as 17-0-0-17, are convenient formations to manufacture for use in the methods of this invention. They have the highest solute concentrations obtainable—approximately 90 percent urea and sulfuric acid—for compositions within the desired range having reasonably low crystallization points, e.g., 50° F. Deviation from the exact 1/1 adduct, e.g., to the 17-0-0-17 formulation, is sometimes desired for manufacturing convenience as discussed hereinafter. While the 17-0-0-17 formulation has a urea-sulfuric acid molar ratio of approximately 1.05/1, that ratio is sufficiently close to the preferred ratio of 1/1 to bring the formulation within the most preferred composition range.

The minor compromise in urea/sulfuric acid molar ratio represented by the manufacture or use of the 18-0-0-17 and 17-0-0-17 formulations is sometimes justified by the fact that compositions having 50° F. crystallization temperatures 1and 1/1 urea/sulfuric acid molar ratios contain only about 85 weight percent solute. Thus, the use of compositions having molar ratios slightly above the optimum value of 1 allows the production of compositions closer to the eutectic point having the same crystallization temperature and approximately 5 percent higher solute concentration.

The urea-sulfuric acid component can be produced by the reaction of urea and sulfuric acid and, optionally water, by either batch or continuous processes. The more concentrated solutions, i.e., those containing less than 25 weight percent, preferably less than 15 weight percent water, are particularly preferred for purposes of manufacture storage and shipment. Also, the urea-sulfuric acid component is preferably substantially or completely free of decomposition products of urea and/or sulfuric acid such as sulfamic acid, ammonium sulfamate, ammonium sulfate, etc., to assure that the preferred compositions employed in the methods of this invention are also free of such decomposition products. The absence of decomposition products in the urea-sulfuric acid component also assures that the sulfuric acid activity of that component has not been degraded by decomposition. Decomposition of the sulfuric acid decreases the amount of acid in the urea-sulfuric acid component available to combine with the urea to form the herbicidally active monourea-sulfuric acid adduct. Sulfuric acid decomposition also reduces the amount of acid available to perform other beneficial functions such as the neutralization of soil alkalinity, improvement of nutrient availability to plants, etc. Urea-sulfuric acid components free of decomposition products can be produced by the reaction of urea and concentrated sulfuric acid by the methods described in my copending application Ser. No. 318,629 filed Nov. 5, 1981, the disclosure of which is incorporated herein by reference.

The monourea sulfuric acid adduct contained in the urea-sulfuric acid component employed in the methods of this invention is the most active form of the urea-sulfuric acid combination for the control of plant suckers. The diurea-sulfuric acid adduct exhibits much less, if any, contact herbicidal activity. Although excess sulfuric acid, i.e., free sulfuric acid, does exhibit some herbicidal activity, it is less active than an equivalent amount of sulfuric acid combined with urea to form the monourea-sulfuric acid adduct. Accordingly, the most preferred compositions are those in which essentially all of the urea and sulfuric acid are present as the monourea-sulfuric acid adduct. Such compositions have a urea/sulfuric acid molar ratio of 1/1. Compositions containing substantial amounts of either the diurea adduct or free sulfuric acid can be employed although they are not as active as the compositions having urea/sulfuric acid molar ratios of 1/1 in the methods of this invention.

As indicated above, unreacted, free sulfuric acid is undesirable in most cases since it is not as effective for the control of parasitic plant suckers as is the monourea adduct on an equivalent acid basis. Also, free sulfuric acid is more corrosive to equipment and human skin and thus is more difficult to handle. The free acid also can react chemically with other components of the compositions employed in this invention such as surfactants, plant nutrients, soil adjuvants, and the like. Thus, the preferred urea-sulfuric acid compositions are those in which at least about 75, usually at least about 85, and most preferably at least about 90 percent of the sulfuric acid is present as the mono- and/or diurea-sulfuric acid adduct. Particularly preferred compositions are those that contain essentially no free sulfuric acid; thus, essentially 100 percent of the sulfuric acid is preferably combined with urea as the mono-and/or diurea adduct. Furthermore, since the monourea adduct is the most active combined form of urea and sulfuric acid, at least about 25, usually at least about 50, preferably at least about 70, and most preferably about 80 to about 100 percent of the sulfuric acid is present as the monourea-sulfuric acid adduct.

The monourea-sulfuric acid adduct is sufficiently active to control plant suckers even when it is employed in very dilute aqueous solutions, and it can be used to control plant suckers on a variety of vegetation even in the absence of other herbicides.

For instance, the 17-0-0-17 composition which contains about 85 weight percent urea and sulfuric acid on a combined weight basis, can be diluted by as much as 200 to 1 with water to produce herbicidally active solutions containing less than 0.5 weight percent solute. Even higher dilution ratios can be employed but are not preferred due to the difficulty involved in applying a sufficient amount of the active monourea adduct to the plant sucker with extremely dilute solutions.

Although the monourea adduct appears to dissociate to urea and sulfuric acid in solutions containing significantly less than about 0.5 weight percent combined urea and sulfuric acid, the dissociated components recombine to form the active adduct on the foliage of treated vegetation. This is apparently due to water evaporation and consequent concentration of the urea and sulfuric acid.

Very low monourea adduct concentrations, e.g., 0.2 percent, or less, do not allow for sufficient dosage rates to provide adequate control of plant suckers in many instances. Thus, the applied solutions will usually contain at least about 0.5, generally at least about 1, preferably at least about 5, and most preferably at least about 10 weight percent urea and sulfuric acid based on the combined weight of those two components.

The concentrated solutions, e.g., those having urea-sulfuric acid concentrations of 85 percent or higher, are very active sucker control agents. However, they are difficult to apply evenly over the foliage due to the relatively low dosage rates required and to their relatively high viscosity.

With these factors in mind, the applied solution will usually contain about 0.5 to about 90, normally about 1 to about 90, and preferably about 5 to about 80 weight percent urea and sulfuric acid on a combined weight basis.

It is preferable to manufacture solutions containing relatively high concentrations of urea and sulfuric acid in order to avoid handling and transporting significant amounts of water. Thus, the liquid compositions, as produced, usually contain at least about 50 and preferably at least about 70 weight percent urea and sulfuric acid on a combined weight basis.

The useful and preferred concentrations of urea and sulfuric acid, and of the mono- and diurea adducts relative to each other, can also be expressed in terms of the urea/sulfuric acid molar ratio. This ratio will be the same in the solid compositions useful in this invention as it is in aqueous solutions of the urea-sulfuric acid component, and will usually be within the range of about $\frac{1}{4}$ to about 7/4, preferably about $\frac{1}{2}$ to about 3/2, and most preferably about 1/1 to about 3/2. Urea/sulfuric acid molar ratios within the range of about 1/1 to about 3/2 define compositions containing essentially no uncomplexed sulfuric acid in which at least 50 percent of the sulfuric acid is present as the monourea-sulfuric acid adduct.

A composition having a urea/sulfuric acid molar ratio of 3/2 contains 3 moles of urea for every 2 moles of sulfuric acid. Assuming complete reaction between the urea and sulfuric acid (which is essentially always the case), 50 percent of the sulfuric acid is present as the diurea-sulfuric acid adduct and 50 percent is present as the monourea adduct. Similarly, in a composition having a urea/sulfuric acid ratio of $\frac{1}{2}$, 50 percent of the sulfuric acid is present as the monourea-sulfuric acid adduct and 50 percent is unreacted "free" acid.

The compositions employed in the methods of this invention may also contain one or more surfactants. Surfactants increase the activity of the urea-sulfuric acid component for the control of plant suckers and broaden the variety of plant suckers that can be controlled by the methods of this invention. Surfactants increase the wetting ability of the liquid urea-sulfuric acid compositions for plant foliage, particularly for the foliage of plants such as citrus plants that are coated with a significant amount of waxy cuticle, and facilitate the distribution of those compositions to treated foliage and to the soil by spraying or by other means.

Preferably, the selected surfactant is sufficiently chemically stable in the urea-sulfuric acid composition to assure that the surfactant retains its wetting ability for the period of time required to manufacture, store, transport, and/or apply the composition. The stability of any surfactant can be readily determined by adding an amount of the surfactant to the urea-sulfuric acid composition in which it is to be employed, and monitoring the combination by nuclear magnetic resonance (NMR). NMR can be used to monitor the frequency and magnitude of spectral peaks characteristic of a selected nucleus, e.g., a hydrogen nucleus, in the subject molecule; i.e., in the surfactant. Persistent spectral peak magnitude and frequency over a period of 5 to 6 hours indicate stability. Diminished magnitude or a shift in peak frequency associated with the selected nucleus indicates instability, i.e., that the arrangement of functional groups in the surfactant molecule has been modified.

Illustrative of classes of stable surfactants are nonionics such as the alkylphenol polyethylene oxides, anions such as the long-chain alkyl sulfates, and cationics such as 1-hydroxyethyl-2-heptadecenyl gloxalidin. Of these, the polyethylene oxide nonionic surfactants are particularly preferred. Illustrative of preferred specific surfactants is the nonionic surfactant marketed by Thompson-Hayward, Inc., under the trademark T-MULZ 891.

The surfactant concentration should be sufficient to increase the foliage wetting ability of the aqueous solution will usually be at least about 0.05, generally at least about 0.1 and preferably at least about 0.2 weight percent of the aqueous solution as applied. Surfactant concentrations of about 0.2 to about 1 weight percent are adequate in most applications.

The urea-sulfuric acid compositions employed in the methods of this invention can also contain any one or more of the known major and minor plant nutrients and/or soil adjuvants such as phosphorus (from phosphoric acid), magnesium, manganese, potassium, zinc, boron, etc., derived from the respective oxides, hydroxides, sulfates, nitrates and the like. They may also contain nitrogen and/or sulfur in addition to that present in the urea and sulfuric acid. Illustrative of other forms of nitrogen and sulfur that can be used are the nitrates such as magnesium nitrate, ammonium compounds such as ammonium phosphate, sulfates such as potassium and ammonium sulfate, and the like. The concentration of these additional major and minor nutrients in the compositions employed in the methods of this invention should be sufficient to introduce the desired amount of the selected nutrients into the soil.

Taking all of the aforegoing factors into account, the liquid urea-sulfuric acid compositions employed in the methods of this invention will comprise about 0.5 to about 90, generally about 1 to about 90, and preferably about 5 to about 80 weight percent of the combination of urea and sulfuric acid (on a dry-weight basis); and, optionally, at least about 0.5, generally at least about 0.1, and preferably at least about 0.2 weight percent of one or more surfactants that are chemically stable in the composition. The lower concentrations of the urea-sulfuric acid component are sometimes preferred for the treatment of plant suckers, and the higher concentrations are preferred for manufacture, transport and storage. Higher concentrations of the surfactant component are preferred in the concentrated solutions of the urea-sulfuric acid component to assure the presence of effective concentrations of all components if the composition is diluted with water prior to application.

The liquid urea-sulfuric acid compositions employed in the methods of this invention can be produced by any method capable of producing a solution of the desired composition. Thus, the surfactant and/or other components, when used, can be added to the concentrated urea-sulfuric acid solution during or immediately after its manufacture by the process described in my copending application Ser. No. 318,624, referred to above, or they can be added to the diluted urea-sulfuric acid solution prior to application. Alternatively, the optional components can be mixed with the amount of water required to produce a concentrated or dilute aqueous solution, as desired before or concurrently with the concentrated aqueous urea-sulfuric acid component.

In accordance with the novel methods of this invention, parasitic plant suckers growing from desired, established plants are controlled by selectively contacting the foliage of the plant sucker with an aqueous solution of the urea-sulfuric acid component at a dosage rate sufficient to apply a herbicidally effective amount of the monourea adduct of sulfuric acid. The urea-sulfuric acid solutions useful in the methods of this invention should be selectively applied by directed spray or by other means capable of contacting only to the foliage and/or the immature stalk of the plant sucker. The method of application should be sufficiently selective to avoid contact of a significant amount of the aqueous solution with the foliage of the established plant which is not associated with the plant sucker. Contact of the aqueous urea-sulfuric acid solutions employed in the methods of this invention with the woody parts of the desired plant will not result in significant damage to the desired plant growth since the woody parts of such plants are resistant to the herbicidal activity of such solutions. Furthermore, the herbicidally active urea-sulfuric acid component is not translocated to the desired portion of the treated plant by transpiration or other mechanism. The translocated urea and sulfuric acid reach the desired growth portion of the treated plant as urea, nitrates and sulfates, and thus directly contribute to the desired growth of the plant.

The amount of the aqueous solution contacted with the plant sucker is preferably sufficient to cover a substantial portion of the foliage and/or stem of the plant sucker in order to assure a more adequate control of the parasitic growth. Application rates of the urea-sulfuric acid solutions useful in the methods invention will, of course, vary significantly on a per acre basis depending upon the number and size of plant suckers which must be controlled. However application rates will usually correspond to about 1 to about 100, generally about 1 to about 50, preferably about 1 to about 20, and most often about 2 to about 10 gallons per acre of the concentrated urea-sulfuric components described above which contain about 75 weight percent or more of a combination of urea and sulfuric acid. Since the concentrated urea-sulfuric acid solutions can be diluted with water to facilitate application and improve coverage of treated foliage, the total volume of diluted solution applied will be within the range of about 1 to about 1,000, usually about 1 to about 500, and preferably about 1 to about 100 gallons of spray volume per acre. These dosage rates correspond to about 10 to about 1,000, usually 10 to about 500, preferably 10 to about 200, and most preferably 20 to about 100 pounds per acre based on the combined weight of urea and sulfuric acid. Since the monourea-sulfuric acid adduct is the most active component of the urea-sulfuric acid solutions employed in the methods of this invention, the most significant consideration in determining effective dosage rates is the determination of the amount of the monourea-sulfuric acid adduct applied to the plant suckers to be controlled. Thus, higher total dosage rates are required when using compositions in which only a portion of the sulfuric acid is present as the monourea-sulfuric acid adduct to accomplish the same degree of control that can be achieved by the use of compositions in which essentially all of the sulfuric acid is present as the monourea adduct.

Although the dosage rate of the urea-sulfuric acid component required to accomplish the desired control will generally be within the ranges discussed above, the dosage rate best suited to accomplish the desired control of plant suckers in any given case, also can be determined by field testing. Such tests may involve the application of a series of compositions having different concentrations of the urea-sulfuric acid component, and/or a series of tests in which the same composition is applied to plant suckers in different plots of the same plant population at different dosage rates, and observing the extent of plant sucker control in each case. When effective concentrations and dosage rates are employed, significant necrosis and plant wilting are evident within 1 hour or less and will provide an adequate indication of effectiveness. The full extent of plant kill will usually be apparent within approximately 2 to 24 hours. In most situations, prescreening tests of that duration are not inordinant. Adequate control is clearly indicated within 24 hours by the disappearance, darkening and/or desiccation of the treated plant tissue. The speed and degree of vegetation control increase as dosage rate is increased, and the dosage rate of the urea-sulfuric acid component is the primary variable in this regard so long as the applied volume is not so high that significant runoff occurs from the treated foliage.

The sray distribution of the urea-sulfuric acid component solutions should be closely controlled to avoid contact of the urea-sulfuric acid component with a significant portion of the foliage of the desired plant growth. Several directed spray techniques which can be used to achieve the selective application of the urea-sulfuric acid solutions are well known in the art. Hand held sprayers are particularly useful for this purpose. However, trailer or tractor mounted boom sprayers, which are adjusted to apply the spray only to the lower portion of established crops, e.g., to a maximum elevation of about two feet above ground level, enable much higher application rates and provide a degree of control which is adequate to avoid contact of the urea-sulfuric acid solution with desired foliage in many types of applications. For instance, directed boom sprayers are particularly useful for the treatment of plant suckers on trellace-trained vines such as berry and grape crops in which the desired producing portion of the vine is located two or more feet above ground level, and in established orchards in which the application of the urea-sulfuric acid solutions at elevations of about 2 foot or less above ground would contact only plant suckers growing from the roots or lower plant extremeties and the woody parts of the established plant.

The methods of controlling plant suckers of this invention have numerous advantages over methods otherwise available to the art. They provide almost immediate control of parasitic plant suckers growing from the lower extremeties of desired ornamental or fruit producing vegetation with little or no toxic effect to the established ornamental or crop plant. In fact, the translocation of the urea-sulfuric acid component to the desired portion of the treated crop plant via the stem of the parasitic sucker, contributes nutrient nitrogen and sulfur to the desired plant parts. The methods of this invention affect only the vegetation contacted and thus, by judicious use of directed spray techniques they can be used to control only parasitic plant sucker growth on established producing plants even in close proximity to the established plants. Application of the urea-sulfuric acid compositions employed in the methods of this invention to the woody part of the established plants does not deter or otherwise effect the growth of the desired vegetation. These methods do not result in the introduction of toxic materials to the environment or to food crops in the treated area and they are less toxic to personnel involved in their application than are compositions employed in alternative methods of controlling parasitic plant suckers. In addition to being less toxic to desired vegetation and to the environment than are alternative methods, the novel methods of this invention are more effective in controlling plant suckers than are many alternatives such as methods which involve the use of spray oils and sulfuric acid. In addition to these advantages, the methods of this invention further result in the addition of significant amounts of nutrient nitrogen and sulfuric acid to the desired plant growth and to the immediate vicinity of the established crop, thus, the methods of this invention contribute significantly to the nutrient supply to the established crop.

Since the urea-sulfuric acid components of the compositions employed in the methods of this invention are free of decomposition products of urea and/or sulfuric acid, including decomposition products of the urea-sulfuric acid adducts, the sulfuric acid value of the compositions employed in these methods is not depleted. Thus, these methods result in the addition of the maximum amount of sulfuric acid to the plants and to the soil for any given dosage rate of the specific composition. Furthermore, the absence of decomposition products in the compositions employed in the methods of this invention assures that these methods will not result in the addition of toxic materials such as sulfamic acid, ammonium sulfamate, and other potentially toxic decomposition products of urea and/or sulfuric acid.

The invention is further described by the following examples which are illustrative of specific modes of practicing the invention and are not intended as limiting the scope of the invention as defined by the appended claims.

EXAMPLE 1

Root-born suckers approximately ½ to 6 inches in height on trellaced chardonnay grapes in which the major vegetative growth is suspended at least three feet above ground level by a trellace framework, are controlled by directed spray application of five gallons per acre of a urea-sulfuric acid composition having the formulation 18-0-0-17 diluted with 4 volumes of water per volume of 18-0-0-17 to produce a total spray volume of 25 gallons per acre having the formulation 3.6-0-0-3.4. The spray solution is applied by a tractor-mounted boom sprayer which directs the spray toward each vine stalk from ground level to a maximum height of about 1 and ½ feet or less above ground level. Ground areas between vine stalks are not sprayed. All plant suckers are completely killed within 24 hours of spraying as evidenced by wilting and degeneration of the plant sucker tissue. No damage results to the established grape vine, foliage or fruit.

EXAMPLE 2

Root-born plant suckers on 8 year old navel orange trees planted on 30 foot centers are completely eliminated by directed spray application to the lower two foot section of each tree trunk and to the ground in the immediate vicinity of each trunk of a solution formed by diluting a urea-sulfuric acid solution in accordance with this invention having the formulation 17-0-0-17 diluted with four volumes of water per volume of 17-0-0-17. A total dosage rate of 10 gallons per acre of 17-0-0-17 (50 gallons per acre total spray volume of diluted solution) eliminates all root-born suckers within 48 hours of application.

While particular embodiments of the invention have been described, it will be understood, of course, that the invention is not limited thereto since many obvious modifications can be made and it is intended to include within this invention any such modifications as will fall within the scope of the appended claims.

Having described my invention, I claim:

1. A method for selectively controlling plant suckers growing from a desired plant without damaging the remainder of said desired plant, which method comprises the steps of: contacting said plant sucker with an aqueous solution comprising a herbicidally effective amount of urea and sulfuric acid, in which solution the molar ratio of said urea to said sulfuric acid is within the range of about ¼ to about 7/4, and avoiding the contact of said aqueous solution with the foliage of said desired plant which is not associated with said plant sucker.

2. The method defined in claim 1 wherein said desired vegetation is selected from the group consisting of deciduous, perenial ornamental and fruit-bearing trees and vines, and combinations thereof.

3. The method defined in claim 1 wherein said desired vegetation is selected from the group consisting of deciduous, perenial, ornamental and fruit-bearing trees and vines, and combinations thereof, growing from root stock that is dissimilar to said desired vegetation, and at least some of said plant suckers are growing from said root stock.

4. The method defined in claim 1 wherein said desired vegetation is selected from the group consisting of fruit-bearing trees, ornamental trees, and trellace-trained fruit-bearing and ornamental vines, and combinations thereof.

5. The method defined in claim 1 wherein said aqueous solution is free of decomposition products of urea and sulfuric acid.

6. The method defined in claim 1 wherein said aqueous solution is free of sulfamic acid and ammonium sulfamate.

7. The method defined in claim 1 wherein said urea and sulfuric acid, in combination, constitute about 2 to about 90 weight percent of said aqueous solution, the molar ratio of said urea to said sulfuric acid is within the range of about ½ to about 3/2, at least about 50 percent of said sulfuric acid is present as the monourea adduct of sulfuric acid, and said solution is contacted with the foliage of said plant suckers at a dosage rate corresponding to about 1 to about 1,000 gallons per acre of said aqueous solution and about 10 to about 1,000 pounds per acre of said combination of urea and sulfuric acid.

8. The method defined in claim 1 wherein said urea and sulfuric acid, in combination, constitute at least about 5 weight percent of said aqueous solution, and said aqueous solution further comprises at least about 0.05 weight percent of a surfactant.

9. The method defined in claim 1 wherein said desired vegetation is selected from the group consisting of fruit-bearing and ornamental trees, trellace-trained fruit-bearing and ornamental vines, and combinations thereof, said urea and sulfuric acid, in combination, constitute at least about 5 weight percent of said aqueous solution, and the molar ratio of said urea to said sulfuric acid in said aqueous solution is within the range of about ½ to about 3/2.

10. The method defined in claim 1 wherein said desired vegetation comprises trellace-trained grape plants.

11. A method for controlling plant suckers growing from desired vegetation which vegetation is selected from the group consisting of desiduous, perenial, ornamental and fruit-bearing trees and trellace-trained vines, and combinations thereof, which method comprises the steps of contacting the foliage of said plant suckers with an aqueous solution comprising the reaction product of urea and sulfuric acid, and avoiding the contact of said aqueous solution with the foliage of said desired vegetation which is not associated with said plant sucker, wherein said urea and said sulfuric acid, in combination, constitute at least about 5 weight percent of said solution, the molar ratio of said urea to said sulfuric acid in said solution is within the range of about ½ to about 3/2, and said aqueous solution is applied to said foliage of said plant sucker at a dosage rate sufficient to contact a substantial proportion of the foliage of said plant sucker with said aqueous solution.

12. The method defined in claim 11 wherein the molar ratio of said urea to said sulfuric acid is within the range of about 1/1 to about 3/2, and said urea and said sulfuric acid, in combination, constitute at least about 10 weight percent of said solution.

13. A method for controlling plant suckers growing from desired vegetation selected from the group consisting of deciduous, perenial, ornamental and fruit-bearing trees and vines, and combinations thereof, without damaging the remainder of said desired vegetation, which method comprises the steps of: contacting the foliage of said plant suckers with an aqueous solution comprising a herbicidally effective amount of the monourea adduct of sulfuric acid, and avoiding the contact of said aqueous solution with the foliage of said desired vegetation which is not associated with said plant sucker.

14. The method defined in claim 1 wherein said desired vegetation is propagated from root stock that is dissimilar to said desired vegetation, and at least some of said plant suckers are propagated from said root stock.

* * * * *